United States Patent
Malpas et al.

(10) Patent No.: US 9,065,284 B2
(45) Date of Patent: Jun. 23, 2015

(54) INDUCTIVELY POWERED MOBILE SENSOR SYSTEM

(75) Inventors: Simon Charles Malpas, Auckland (NZ); Aiguo Hu, Auckland Central (NZ); David Budgett, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 1658 days.

(21) Appl. No.: 11/575,449

(22) PCT Filed: Sep. 16, 2005

(86) PCT No.: PCT/NZ2005/000245
§ 371 (c)(1),
(2), (4) Date: Aug. 21, 2007

(87) PCT Pub. No.: WO2006/031133
PCT Pub. Date: Mar. 23, 2006

(65) Prior Publication Data
US 2007/0296393 A1    Dec. 27, 2007

(30) Foreign Application Priority Data

Sep. 16, 2004   (NZ) .................................. 535390

(51) Int. Cl.
*H02J 17/00* (2006.01)
*H02J 5/00* (2006.01)
*A61B 5/00* (2006.01)

(52) U.S. Cl.
CPC .............. *H02J 5/005* (2013.01); *A61B 5/0002* (2013.01); *A61B 2560/0219* (2013.01)

(58) Field of Classification Search
CPC .................................. H02J 5/005; H02J 17/00
USPC .......................... 307/104, 149, 151; 320/108
See application file for complete search history.

(56) References Cited

U.S. PATENT DOCUMENTS

| 4,496,896 | A | * | 1/1985 | Melocik et al. ............... 320/108 |
| 5,455,467 | A | * | 10/1995 | Young et al. .................. 307/104 |

(Continued)

FOREIGN PATENT DOCUMENTS

| DE | 20016655 U1 | * | 2/2002 |
| DE | 10221484 A1 | * | 11/2003 |

(Continued)

OTHER PUBLICATIONS

Machine translations for DE20016655U1 and DE10221484A1.*

(Continued)

*Primary Examiner* — Fritz M Fleming
(74) *Attorney, Agent, or Firm* — Law Office of Richard F. Jaworski PC

(57) ABSTRACT

The present invention provides an inductively powered sensor system having a primary conductive path capable of being energized to provide an electromagnetic field in a defined space. An inductive power pick-up is associated with a sensor and is capable of receiving power from the field to supply the sensor. The system includes a first sensing unit to sense the power available to the pick-up and a control unit to increase or decrease the power available to the sensor dependant on the sensed power available. A method of inductively powering a sensor, an inductively powered sensor and an animal enclosure including one or more primary conductive path of an inductive power supply are also disclosed.

24 Claims, 7 Drawing Sheets

(56) References Cited

U.S. PATENT DOCUMENTS

| | | | |
|---|---|---|---|
| 5,517,194 A | 5/1996 | Carroll et al. | |
| 5,876,425 A | 3/1999 | Gord et al. | |
| 6,047,214 A * | 4/2000 | Mueller et al. | 607/61 |
| 6,184,651 B1 * | 2/2001 | Fernandez et al. | 320/108 |
| 6,212,430 B1 * | 4/2001 | Kung | 607/61 |
| 6,307,468 B1 | 10/2001 | Ward, Jr. | |
| 6,345,203 B1 | 2/2002 | Mueller et al. | |
| 6,364,735 B1 * | 4/2002 | Bristow et al. | 446/397 |
| 6,442,434 B1 | 8/2002 | Zarinetchi et al. | |
| 6,597,076 B2 * | 7/2003 | Scheible et al. | 307/104 |
| 6,803,744 B1 * | 10/2004 | Sabo | 320/108 |
| 7,355,150 B2 * | 4/2008 | Baarman et al. | 219/620 |
| 2003/0014091 A1 * | 1/2003 | Rastegar et al. | 607/61 |
| 2003/0069051 A1 | 4/2003 | Pretre et al. | |
| 2003/0078634 A1 * | 4/2003 | Schulman et al. | 607/61 |
| 2003/0114769 A1 | 6/2003 | Loeb et al. | |
| 2004/0130915 A1 * | 7/2004 | Baarman | 363/21.02 |
| 2004/0130916 A1 * | 7/2004 | Baarman | 363/21.02 |
| 2005/0151511 A1 * | 7/2005 | Chary | 320/127 |

FOREIGN PATENT DOCUMENTS

| | | |
|---|---|---|
| WO | 00/56210 | 9/2000 |
| WO | WO 03105308 A1 * | 12/2003 |
| WO | 2004/105208 | 12/2004 |
| WO | 2004/105226 | 12/2004 |
| WO | WO-2004/105208 A1 | 12/2004 |
| WO | WO-2005/000391 A1 | 1/2005 |

OTHER PUBLICATIONS

PCT International Application for International Application No. PCT/NZ2005/000245, dated Nov. 22, 2005.

* cited by examiner

INDUCTIVELY POWERED MOBILE SENSOR SYSTEM

CROSS-REFERENCE TO RELATED APPLICATIONS

This is a U.S. National Phase application under 35 U.S.C. 371 of International Patent Application No. PCT/NZ2005/000245, filed on Sep. 16, 2005, which claims priority to New Zealand Patent Application No. 535390, filed on Sep. 16, 2004. The International Application was published on Mar. 23, 2006 as WO 2006/031133 A1 under PCT Article 21(2).

FIELD OF THE INVENTION

This invention relates to inductive supply of power to mobile sensors. The invention has particular application to a wireless power supply for biosensors that are implanted in living creatures (including humans) and transmit data representative of the physiological parameters to a receiver through a wireless link.

BACKGROUND

Physiological parameters in animals are measured using sensors which are placed near, on or under the skin. Wires then carry the signal from the sensor to an external amplifier and display unit. This method has a number of undesirable limitations, some of which include: the introduction of movement artefacts; restraints of movement exacerbating an unnatural environment; a potential source of infection, and; reliability problems with wires becoming tangled, breaking, or being bitten.

Some systems presently exist for the wireless monitoring of animals, however these systems have power management problems. Typically, the wireless systems that are presently available require a battery to be provided to power the sensor. This battery must be carried by the animal. The battery is often bulky which can cause difficulties when providing the sensor unit within the animal. Also, there is an inability to remotely undertake long term recordings of physiological parameters because the batteries need to be removed so that they may be replaced or recharged.

Wireless supply of power to biosensors has been attempted, but these systems either require a tightly controlled coupling between the biosensor and power source, or can only supply sufficient power for monitoring slowly changing parameters, such as temperature. Controlling the power transferred to the sensor can be difficult because the power available varies depending on location and orientation of the sensor with respect to the power source. Excess power is dissipated as heat in the sensor. This is obviously highly undesirable causing discomfort or harm to the animal in which the sensor has been implanted, and exacerbating an unnatural environment for the animal.

Contactless power supplies that transfer power inductively have been extensively developed. These have a primary conductive path (usually a cable arranged on an elongate track) which is energised by a power supply to produce an electromagnetic field about the primary path. One or more power pick-ups are provided closely adjacent to the path. Each pick-up has a tuned circuit which receives energy from the field and uses this to supply a load. These power supply systems are typically adapted to supply power over a carefully controlled relatively short air gap of approximately 1 cm.

To power a biosensor, for example in an animal in a defined space such as an enclosure or a cage, the power transfer system must deal with greater physical separation and arbitrary orientation between the primary conductive path and pick-up.

U.S. Pat. No. 6,345,203 discloses magnetic vector steering for powering multiple implant devices. It also refers to communication with an implanted device via the electromagnetic filed which energises the implanted device. The energy status of an implanted device can be monitored. However, this does not address problems with heat dissipation. Furthermore, although the implants are referred to as "arbitrarily oriented", the system relies on a known configuration of implanted devices in relation to the primary coil. The implants are disclosed as being provided in a fixed location with respect to the primary field generating coils. Thus, the problems of variable distance and random orientation of implants in relation to the primary coils are not addressed.

SUMMARY OF THE INVENTION

It is an object of the present invention to provide an improved inductively powered sensor apparatus and/or system.

Alternatively, it is an object of the invention to provide an improved method for supplying power to a sensor.

Alternatively, it is an object of the invention to provide a method, apparatus or system for providing an inductively powered sensor which will at least provide the public with a useful choice.

In a first aspect the invention consists in an inductively powered sensor system, the system including:
  a primary conductive path capable of being energised to provide an electromagnetic field in a defined space,
  an inductive power pick-up associated with a sensor, the pick-up being capable of receiving power from the field to supply the sensor,
  a first sensing means to sense the power available at the pickup from the field,
  control means to increase or decrease the power received at the pick-up dependant on the sensed power available at the pick-up.

Preferably a second sensing means is provided to sense the immediate power requirement of the sensor and wherein the control means to increase or decrease the power available to the sensor so that the power available to the sensor substantially matches the immediate power required by the sensor.

Preferably the control means varies the field by altering the frequency of the field to tune or de-tune the field toward or away from an optimal resonant frequency of the pick-up.

Alternatively the control means varies the field by increasing or decreasing the current or voltage supplied to the primary conductive path.

Alternatively the control means varies the field by varying a vector of the field.

Alternatively the control means varies the optimal resonant frequency of the pick-up.

Alternatively the control means varies the power flow using a combination of the techniques discussed above.

Preferably the first sensing means sense the power available to the pick-up by sensing a voltage provided by the pick-up.

Preferably the second sensing means sense the immediate power requirement of the sensor by sensing a current drawn by the sensor.

Preferably the first sensing means sense the power available to the pick-up by sensing a location of the sensor within the defined space.

Preferably the system includes a transmission means to transmit the immediate power requirement of the sensor to the control means.

Preferably the system includes a transmission means to transmit the power available to the pick-up to the control means.

Preferably the transmission means also transmit physiological data sensed by the sensor.

Preferably the sensor includes a charging means to charge an energy storage device from power supplied by the pick-up, so that power is available to the sensor when power is not supplied by the pick-up.

Preferably the control means provide the field only when the energy storage device requires charging.

Preferably the pick-up includes a plurality of pick-up coils oriented in different directions.

Preferably the sensor includes vector sensing means to sense the orientation of the pick-up relative to a vector of the field.

Preferably a plurality of primary conductive paths are provided to allow the control means to vary the field vector.

Preferably the sensor includes vector sensing means to sense the orientation of the pick-up relative to a vector of the field and the control means varies the field vector dependent on the sensed orientation.

Preferably the control means sweeps the frequency of the field to locate a resonant frequency or near resonant frequency of a pick-up.

Preferably a plurality of primary conductive paths are provided and a plurality of sensors are provided, each sensor having a separate pick-up associated therewith, and the control means varies the field to selectively make power available to each sensor.

Preferably the sensor is a biosensor.

In a further aspect the invention consists in a method of inductively powering a sensor provided in a defined space, the method including:
    generating an electromagnetic field in the defined space,
    sensing the power available to a sensor provided in the defined space, and
    controlling the field to increase or decrease the power available to the sensor dependant upon the sensed power available.

Preferably the method includes sensing the power requirement of the sensor and controlling the field to increase or decrease the power available to the sensor so that the power available to the sensor substantially matches the immediate power required by the sensor.

Preferably the step of varying the field includes the step of increasing or decreasing the frequency of the field.

Preferably the control means varies the field by increasing or decreasing the current or voltage supplied to the primary conductive path.

Preferably the control means varies the field by varying the field vector.

Preferably the sensor includes a charging means to charge an energy storage device from power supplied by the pick-up so that power is available to the sensor when power is not supplied by the pick-up, and the method includes controlling the field to provide power only when the energy storage device requires charging.

Preferably the method includes the step of sensing the orientation of the pick-up relative to a vector of the field.

Preferably the method includes the step of controlling the field vector dependent on the sensed orientation.

Preferably the method includes the step of sweeping the frequency of the field to locate a resonant frequency or near resonant frequency of the pick-up.

Preferably a plurality of primary conductive paths are provided and a plurality of sensors are provided, each sensor having a separate pick-up associated therewith, and the method includes varying the field to selectively make power available to each sensor.

Preferably the sensor is a biosensor.

In a further aspect the invention consists in an inductively powered sensor including
    first sensing means to sense the power available to the sensor from an inductive power pickup, and
    transmission means to transmit sensed information to a remote control device for controlling the power available to the sensor.

Preferably the sensor includes second sensing means to sense the instantaneous power requirement of the sensor for provision to the transmission means.

Preferably the sensor includes vector sensing means to sense the orientation of the pick-up relative to a vector of a field supplying power to the pick-up and provide the sensed information to the transmission means.

Preferably the sensor includes a charging means to charge an energy storage device from power supplied by the pick-up, so that power is available to the sensor when power is not supplied by the pick-up.

Preferably the pick-up includes a plurality of pick-up coils oriented in different directions.

Preferably the sensor is a biosensor.

Preferably the transmission means transmit physiological data sensed by the biosensor.

In a further aspect the invention consists in an animal enclosure having a perimeter defined by one or more walls, floor and/or ceiling and including one or more primary conductive path of an inductive power supply in or about the or any part of the perimeter so that upon the primary conductive path being energised an electromagnetic field is provided within the enclosure.

Preferably the enclosure comprises a cage.

Preferably the enclosure comprises an animal rest area of a larger animal enclosure.

Preferably the enclosure comprises an animal feed station of a larger animal enclosure.

Preferably a plurality of primary conductive paths are provided and are arranged to provide electromagnetic fields having different field vectors.

Preferably the primary conductive path comprises a multi-turn coil.

Preferably the enclosure includes a power supply for energising or controlling energisation of the primary conductive path.

Preferably the enclosure includes a radio frequency receiver for receiving information transmitted by a sensing device.

In a further aspect the invention consists in an inductively powered sensor system, the system including:
    a primary conductive path capable of being energised to provide an electromagnetic field in a defined space,
    an inductive power pick-up associated with a sensor, the pick-up being capable of receiving power from the field to supply the sensor,
    a sensing means to sense the power requirement of the sensor,
    control means to vary the field to increase or decrease the power available to the sensor dependant on the sensed power requirement of the sensor.

According to a further aspect the invention consists of an inductively powered sensor system substantially as herein described with reference to any one of the embodiments shown in the drawings.

According to a further aspect the invention consists of a method of powering a sensor substantially as herein described with reference to any one of the embodiments shown in the drawings.

According to a further aspect the invention consists of an inductively powered sensor substantially as herein described with reference to any one of the embodiments shown in the drawings.

According to a further aspect the invention consists of an animal enclosure substantially as herein described with reference to any one of the embodiments shown in the drawings.

Further aspects of the invention, which should be considered in all its novel aspects, will become apparent to those skilled in the art upon reading the following description which provides at least one example of a practical application of the invention.

BRIEF DESCRIPTION OF DRAWINGS

One or more embodiments of the invention will be described below by way of example only and without intending to be limiting with reference to the following drawings, in which.

DETAILED DESCRIPTION OF PREFERRED EMBODIMENTS

Figure 1:
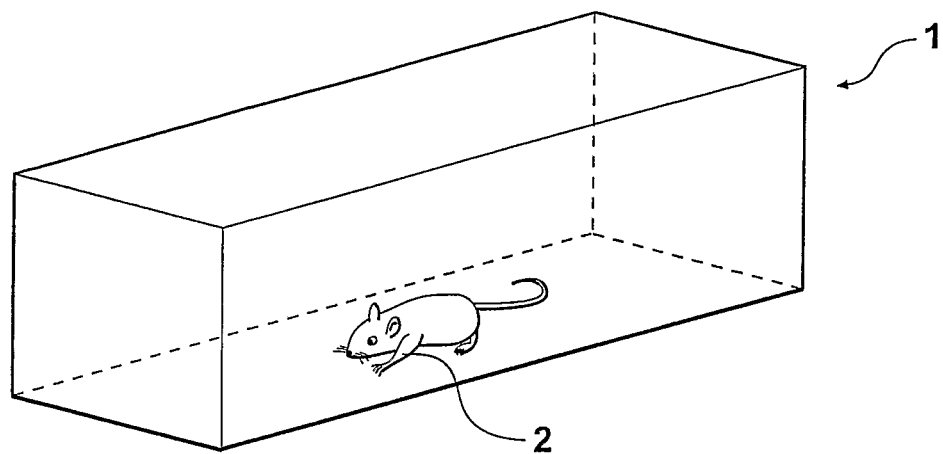
FIG. 1 is a diagrammatic view of an enclosure such as a cage containing an animal.

Referring to FIG. 1, an enclosure in the form of an animal cage is shown generally referenced 1 containing an animal such as a mouse 2. Although the invention will be described with reference to a cage suitable for containing a small animal such as a mouse, those skilled in the art will appreciate that the invention is generally applicable to the wireless supply of power to a very wide range of animals (including humans or other living creatures) within a defined space. Furthermore, although the invention is described below in relation to biosensors, those skilled in the art will realise that the invention is applicable to other sensors.

An electromagnetic field may be established in the space defined by the enclosure by providing an alternating current in a primary conductor adjacent to the cage 1. Electrical energy may be transferred from the field to a tuned inductive pick-up circuit implanted in the animal 2. The pick-up circuit can thus provide the power supply required by a biosensor implanted in the animal.

Figure 2:
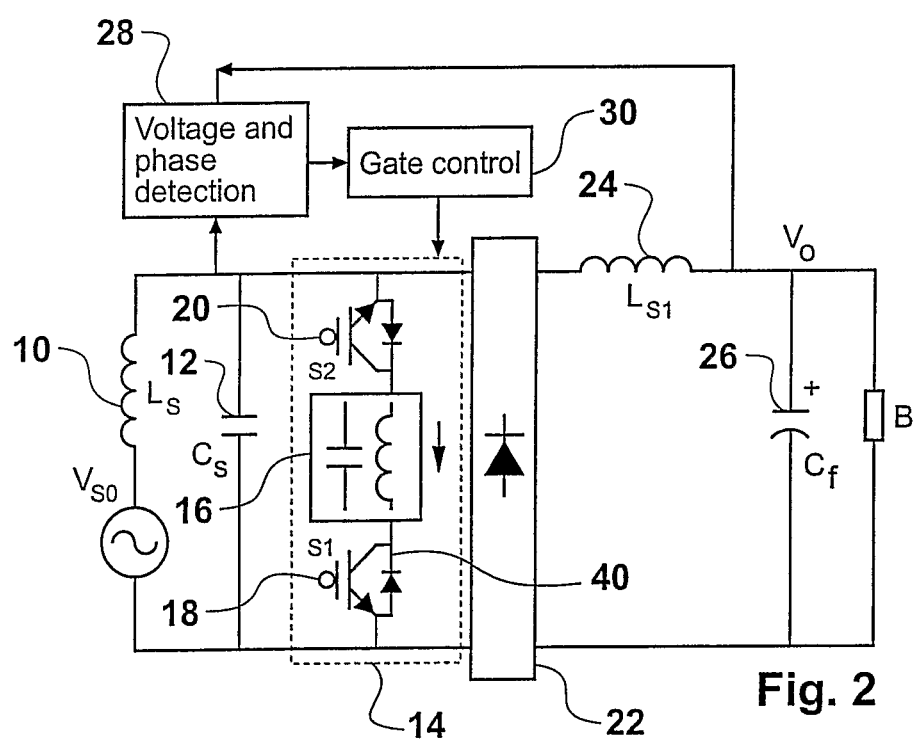
FIG. 2 is a circuit diagram for a power pick-up circuit

We have found that a circuit such as that shown in FIG. 2 may be used in the pick-up to provide a power supply to a biosensor B. The operation of this circuit has been described in our pending international application no. WO2004/105208 the disclosure of which is incorporated herein by reference. In brief, operation of this circuit is as follows. A pick-up coil 10 has a voltage (represented by $V_{SO}$) induced therein when it is in the presence of an appropriate electromagnetic field. A tuning capacitor 12 ($C_S$) has a value chosen to provide a desired resonant frequency so as to optimise the transfer of energy from the electromagnetic field to the pick-up. A rectifier circuit 22 rectifies the current from the resonant circuit and filters it through a DC inductor 24 ($L_{S1}$) and a filter capacitor 26 (CF) to supply the desired output voltage $V_0$. A voltage and phase detection circuit 28 and a gate control circuit 30 control the switches 18 and 20. Modules 28 and 30 may alternatively be implemented in software.

Heat generation in an implanted sensor is highly undesirable. The circuit shown in FIG. 2 includes an optional controlled reactive element 14. This element forms one example of a system capable of preventing heat generation when the power available from the tuned circuit of the pickup system exceeds the power requirements of the load. Element 14 may comprise an inductor or capacitor 16 which is selectively switched into or out of the resonant circuit of the pick-up by control of switches 18 and 20 (S1 and S2). In this way, the resonant frequency of the pick-up can be varied to allow the power received by the pick-up to vary dependant upon the requirements of the load (i.e. the requirements of biosensor B) and the strength of the magnetic field flux experienced by the pickup coil. The circuit shown and described with reference to FIG. 2 effectively eliminates generation of unnecessary heat.

In order to generate a required electromagnetic field in the primary conductor to supply the pick-ups which power the biosensors, a primary power supply is required. We have found that an appropriate supply may be one such as that shown in FIG. 3, the operation of which is described in detail in our pending international patent application no. WO2004/105226 the disclosure of which is incorporated herein by reference. In brief, a DC supply 32 provides a current $I_D$ to a DC inductor 34 and then to inductors 36 and 38 which split the supply. Switches 40 and 42 are switched on alternately to allow the supply to be switched through a resonant circuit comprising a load 44 represented by variable resistance R that has a corresponding inductance represented by inductor 46. A tuning capacitor 48 provides the desired resonant frequency. However, a further reactive element which may comprise an inductor or capacitor (or combinations of these elements) 50 is provided. This element provides a second example of how power flow can be adjusted to match power availability at the pickup to biosensor load requirements to avoid generating heat within the biosensor assembly. For ease of illustration the reactive element 50 is shown as a simple variable inductor or capacitor, but is implemented in practice using semiconductor switches between each terminal of a selected capacitance or inductance and the terminals of tuning capacitor 48.

The variable capacitance or inductance is controlled by voltage and phase detection circuitry 52 and gate drive control circuitry 54 (which may alternatively be implemented using software). In this way the resonance of the resonant circuit can be varied to tune the electromagnetic field to the desired frequency.

The inductor 46 and the load R represent the primary conductor (and its load) which is provided as a coil (either a partial turn, a single turn or most preferably multiple turns). The primary conductor is located about or adjacent to the enclosure 1, and we have found that an electromagnetic field of sufficient strength may be generated within the space to allow the pick-up shown in FIG. 2 to provide a required power supply for a biosensor. For example, the field may be generated at 200 kHz, and the biosensor may require a DC voltage of approximately 3 volts and a continuous current of approximately 10 milliamps. The relatively high field frequency allows physically small components to be used. Also, the detuning control allows some variation in component values, so tolerances are not critical.

The pick-up circuit of FIG. 2 can be provided in relatively small physical form, for example an encased unit small enough to be implanted in relatively small animals such as mice, to allow continuous operation of a biosensor.

The pick-up coil can comprise a partial turn coil, or a single or multiple turn coil and can be formed in a variety of different ways. In one example, the coil may simply comprise a partial turn of conductive material provided on a printed circuit board. In another embodiment, the pick-up may comprise a multi-turn coil mounted on a circuit board, or mounted within a cut out space on a circuit board in order to keep space to a minimum. The coil may also include a material having magnetic properties, for example a ferrite core, to enhance field strength and thus power transfer capacity. In one embodiment the ferrite core may provide a battery housing (if a battery is provided) or facilitate location of the battery or a similar device such as a supercapacitor.

Figure 4:
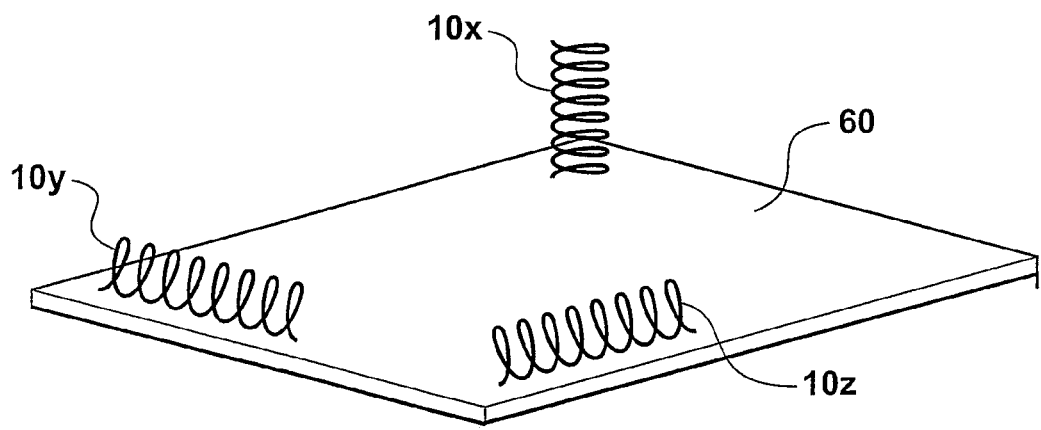
FIG. 4 is a diagrammatic perspective view of three pick-up coils

In another embodiment multiple pick-up coils may be provided. Turning to FIG. 4, a multiple coil pick-up arrangement is shown diagrammatically on a piece of circuit board 60. Pick-up coil 10x is arranged in a vertical direction as shown in FIG. 4. Pick-up coil 10y is arranged in a horizontal direction directed across the page as shown in FIG. 4, and pick-up coil 10z is arranged in a horizontal direction arranged along an axis which runs "in to or out of" the page as shown in FIG. 4. Therefore, the configuration shown provides coils which are mounted perpendicularly to each other so that they have axes corresponding to x, y and z axes of three dimensional space.

Figure 5:
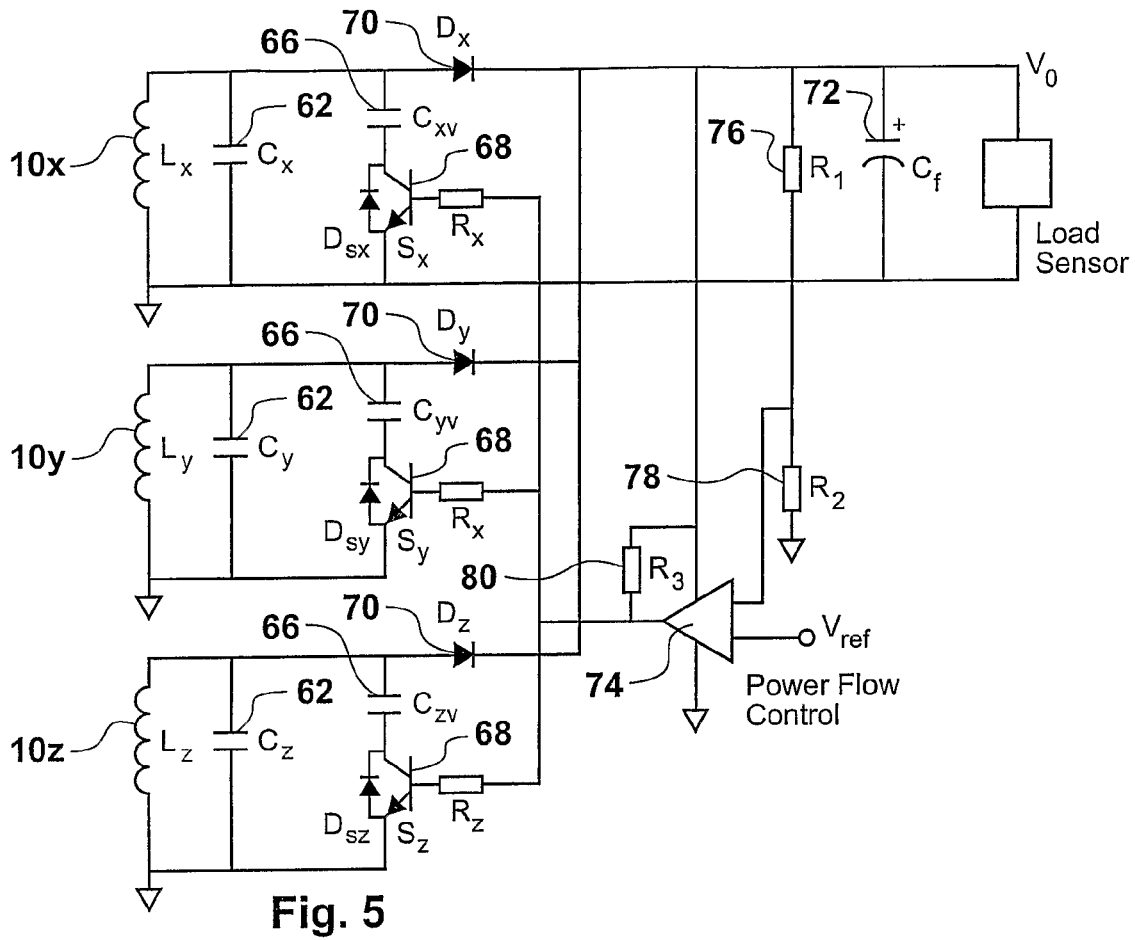
FIG. 5 is a circuit diagram showing pick-up circuit for use with the pick-up coils of FIG. 4

Turning to FIG. 5, a pick-up circuit which may be used with the coils shown in FIG. 4 is illustrated. Referring to that figure, each of the pick-up coils has a tuning capacitance represented by capacitor 62. A further capacitor 66 can be controllably switched in parallel with capacitor 62 by a control transistor 68. The output of the pick-up circuit is rectified by Shottky Diode 70. The output from each of the Shottky Diodes 70 is then provided to a control stage where it is initially filtered by a filter capacitor 72 for provision to the biosensor load B. A comparator 74 and associated resistive network (resistors 76 to 80) controls the natural resonant frequency of each of the pick-up coils by activating or deactivating transistor 68. This allows the power transferred to the pick-ups to be controlled to match the power requirements of the biosensor load B. A single controller is used to control three pick-ups at the same time, so the pick-up size and power losses are smaller than using three separate circuits. The controller may over tune or under tune the pick-up to control the power flow.

Those skilled in the art to which the invention relates will see that the multiple pick-up coil arrangement described above (or even a single pick-up coil arrangement) may be provided using a pick-up circuit that does not include a variable reactive element i.e. a pick-up having a fixed resonant frequency pick-up circuit may be used. Furthermore, coil directional arrangements other than those described above may be used.

Figure 6A:
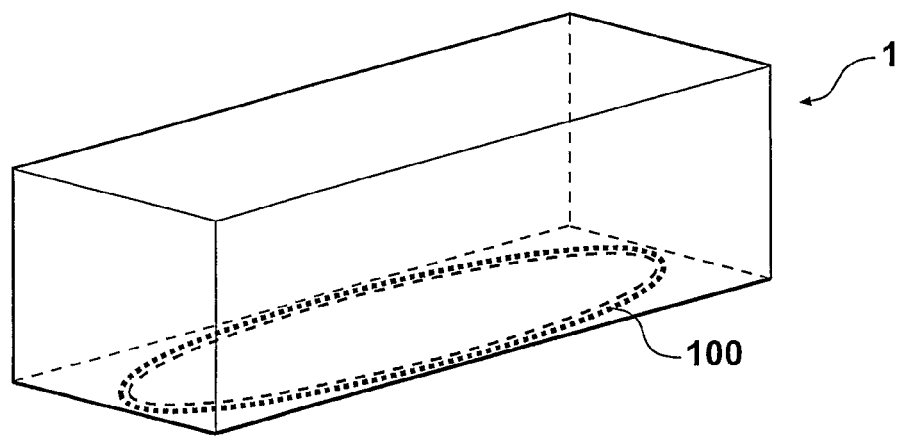
FIGS. 6a-6e show various configurations of conductors arranged about the enclosure of FIG. 1 to provide a magnetic field within the enclosure
Figure 6B:
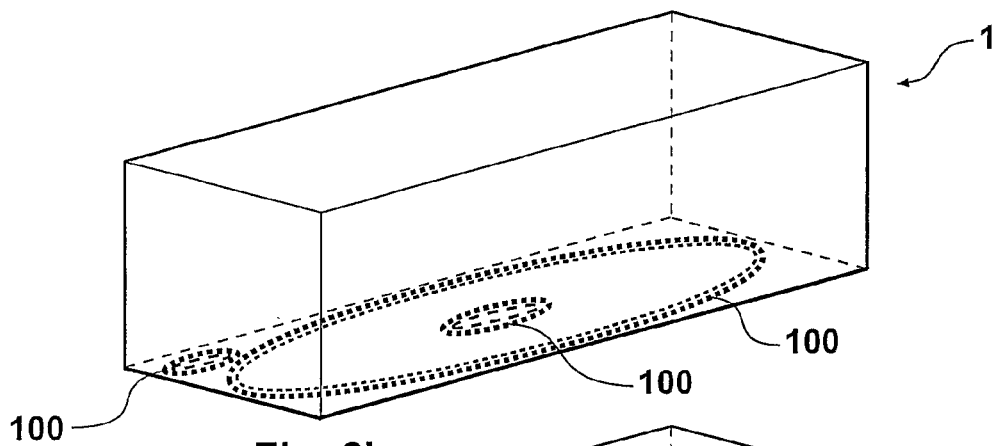
Figure 6C:
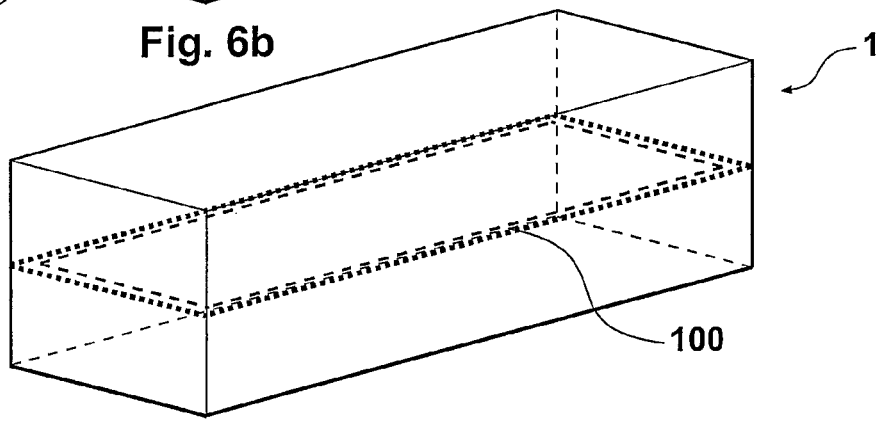
Figure 6D:
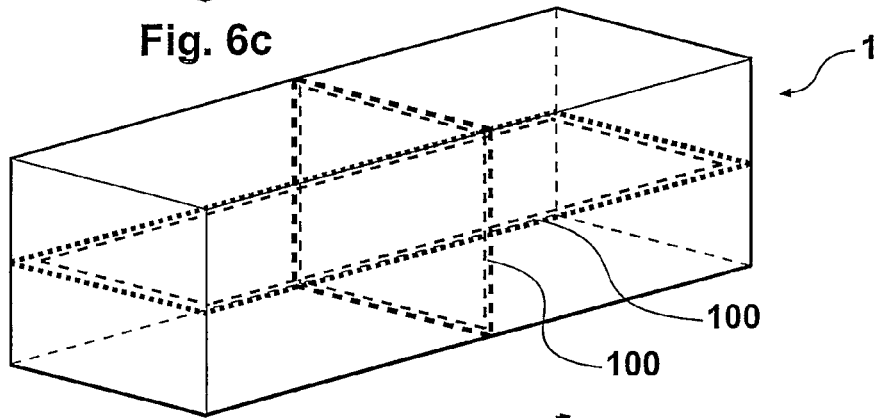
Figure 6E:
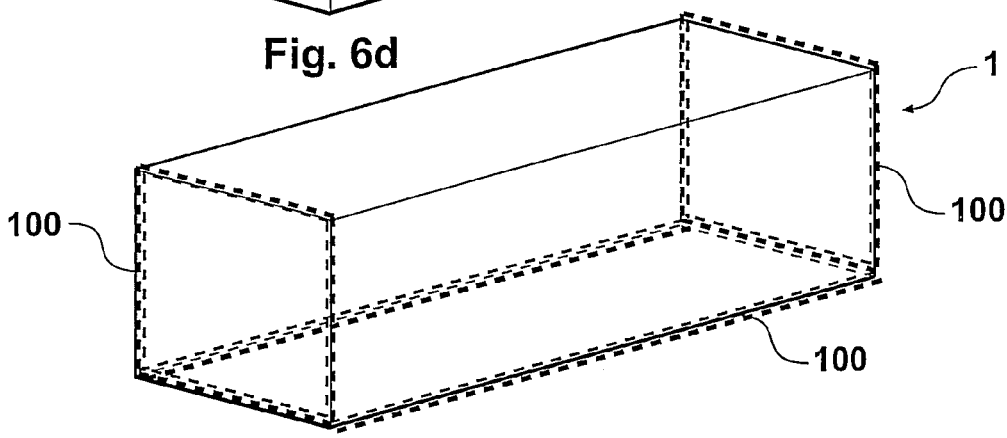
Figure 7A:
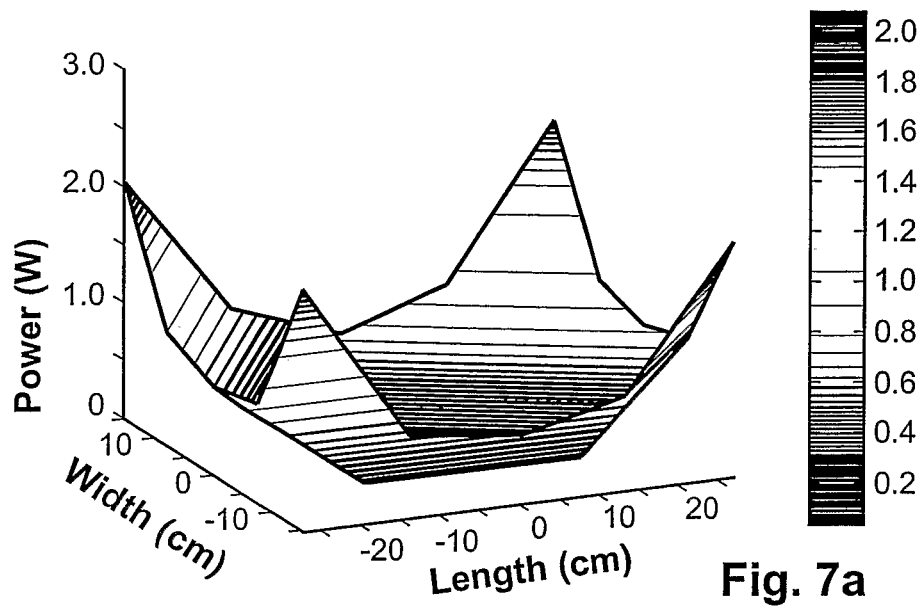
FIG. 7a is a plot of available electrical power in a cross section through the enclosure of FIG. 6c in the same plane as the primary conductor
Figure 7B:
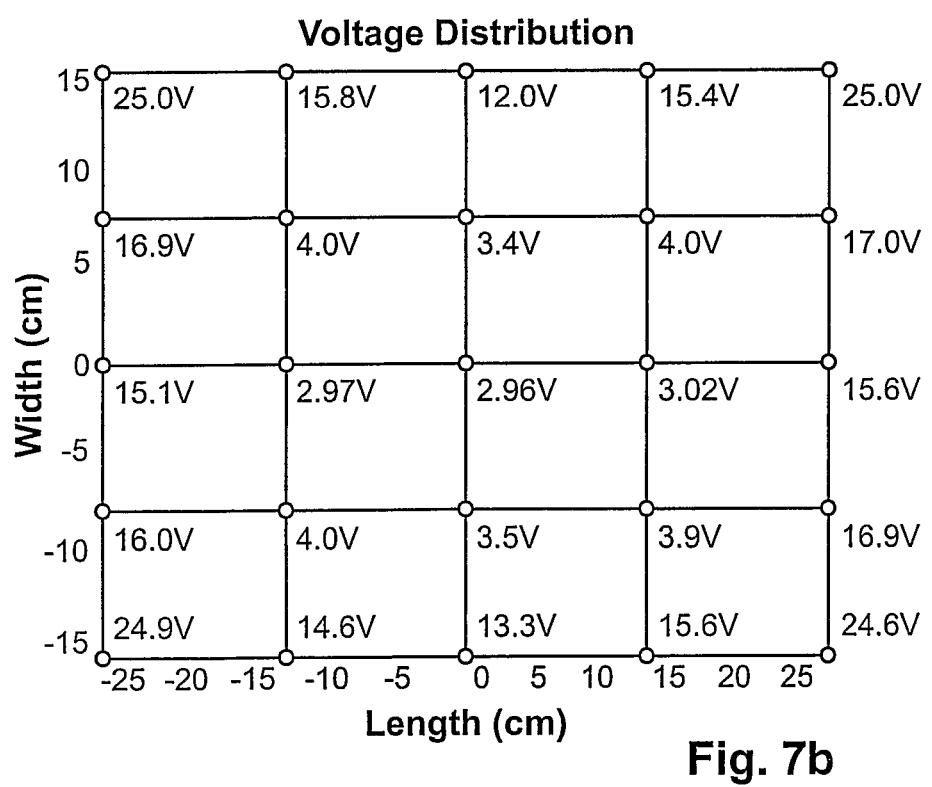
FIG. 7b is a plot of pick-up voltage distribution measured in plan view through the enclosure of FIG. 6c, in the same plane as the primary conductor

Turning to FIGS. 6a to 6e, various arrangements of the primary conductor for providing an electromagnetic field within the enclosure space are shown. The conductors shown in FIGS. 6a to 6e are discussed below with reference to a coil of conductive material. However, those skilled in the art will realise that a partial, single or full turn of conductive material may be provided rather than multiple turns. Referring to FIG. 6a, a coil 100 is shown provided on or within a wall of the enclosure, such as being located externally at the base of the container. In FIG. 6b multiple coils are provided. This allows fields to be provided in localised locations throughout the enclosure. Another arrangement shown in FIG. 6c illustrates a coil mounted externally of the container horizontally about a mid section of the container. In FIG. 6d, the arrangement of FIG. 6c can further include another coil mounted about the mid section of the container but in a vertical plane. In FIG. 6e, coils are shown mounted about the periphery of the base of the container and about the ends of the container. Therefore, coils may be located in a variety of different locations in or about any part of the one or more walls, floor and/or ceiling that define the perimeter of the enclosure. Primary coils may also be located at various locations inside the enclosure. The available electrical power and voltage distribution inside the enclosure and in the same plane as the coil shown in FIG. 6c is shown in FIGS. 7a and 7b respectively.

Figure 3:
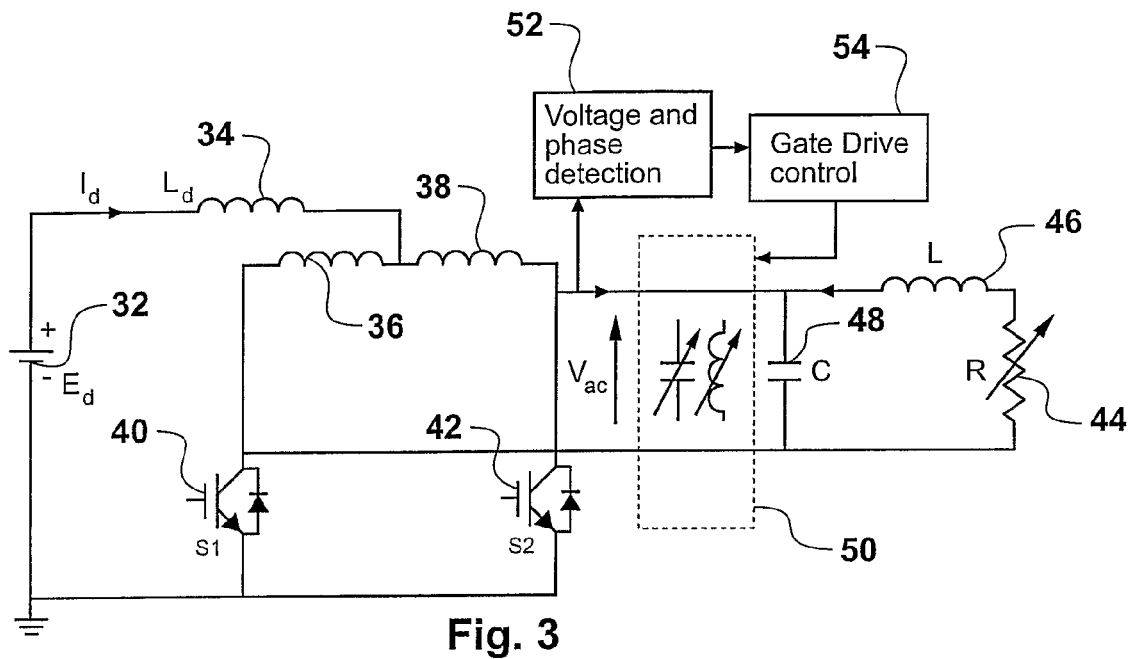
FIG. 3 is a circuit diagram for a power supply
Figure 8:
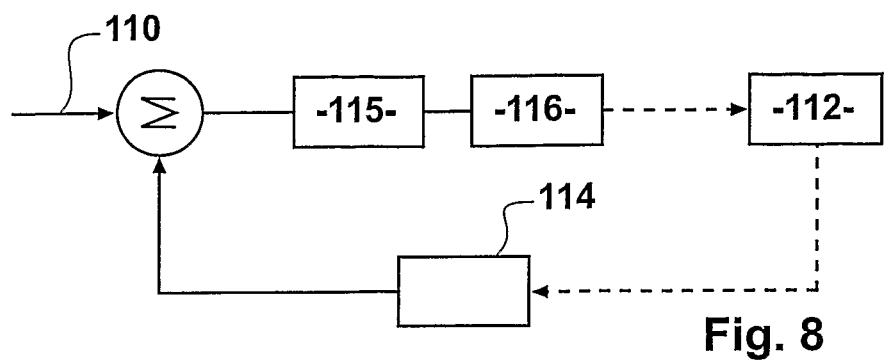
FIG. 8 is a diagram of a control circuit for controlling the field provided in an enclosure such as the enclosure of FIG. 1

The primary circuit, such as that shown in FIG. 3, may be controlled to controllably vary the field based on the instantaneous power requirements of each pick-up. These power requirements may be derived from information retrieved from each pick-up, or based on other information such as location of a pick-up, what the power requirements of the pick-up should be at a given location or at a given time for example, or a combination of these sources of information. Referring to FIG. 8, a feed back control system is diagrammatically illustrated.

Turning to FIG. 8, in this example a control system can be provided which has an input reference signal 110 corresponding to the power required by the biosensor and associated circuitry that the pick-up supplies. The pick-up 112 includes a transmitter (for example a device which transmits RF signals representative of desired information) to transmit a signal representative of the current output voltage of the pick-up to a receiver 114. The received signals are compared with the reference to provide an error signal which is used by controller 115 to control the power supply 116. The power supply may be controlled in a number of different ways. For example, the magnitude of the voltage that the power supply provides to the primary conductor may be increased or decreased to thereby change the field strength within the enclosure and thus vary the output of the pick-up. Therefore power received by the pick-up circuit can be fed back to the primary circuit controller to facilitate adjustment of the electromagnetic field generated to maintain adequate power levels at the pick-up or to reduce the power level at the pick-up to prevent generation of unnecessary heat. Feed back is currently available through the use of a radio transceiver module (based on an integrated circuit part number nRF24E1 from Nordic Semiconductor) with a data bandwidth of 1 Megabit per second and transmitting in the 2.4 GHz frequency spectrum band. This transceiver module is primarily used to digitise and transmit physiological data sensed by the biosensor, but the pick-up power requirement data can also be transmitted using this module, for example by adding more digital data representing power status to the packets being transmitted with digital physiological data. Capacitor buffering of the power supply to the biosensors smoothes out short duration fluctuations such that adequate feedback response time is easily achieved. The actual position or orientation of the pick-ups can also be detected to facilitate the required power flow control.

Alternatively, a feed forward control system may be implemented. For example, the primary circuit controller can monitor the power being delivered to its own primary coil and use this to estimate the power being drawn from the pick-up coil. When the pick-up coil is drawing less power than the level required by the biosensor, a primary control algorithm will attempt to increase power transfer by adjusting the generated field.

Independent pick-up systems (for example multiple animals within the enclosure) can be powered through the primary circuit controller using a time division multiplexing scheme to produce electromagnetic fields appropriate for each pick-up (for example at different frequencies or vectors) at different time slots.

The apparatus and systems described above may be implemented in a variety of different ways. As a first example, a single primary conductor coil may be provided about the enclosure, such as for example is shown in FIG. 6c. The coil is powered by a conventional power supply, although a power supply such as that described with reference to FIG. 3 could be used if desired. The power supply is chosen so that it is sufficient to provide a field throughout the enclosure of sufficient strength to power a pick-up. One or more animals is then provided in the enclosure, each animal having a biosensor device which is powered by a pick-up such as the pick-up described with reference to FIG. 2. The pick-up may also include an energy storage device such as a re-chargeable battery or a supercapacitor to augment the wireless power supply if required. Therefore, if the load cannot be met by the power supply, the battery can assist until such time as the wireless supply is sufficient at which time the battery may begin to be recharged by the wireless supply. For example, the electromagnetic field may be provided in a certain area of the enclosure that is visited frequently, such as a feeding station, and the battery may be recharged while the animal is in that area. Alternatively, normal physiological data acquisition may occur under battery power in the animal's home cage, and the animal relocated to the area containing the magnetic field for battery recharging. As another alternative, the biosensor may operate primarily from the battery, so that the electromagnetic field is only generated when the battery requires charging.

In another example, the primary power supply and primary conductor as described immediately above are provided, but the pick-up device includes the apparatus shown and described in FIGS. 4 and 5. This allows the field to be fully utilised independently of the orientation of the pick-up. The biosensor receives power continuously from the pick-up.

In another example, a pick-up which is tuned to a non-adjustable resonant frequency is used. Such a pick-up can be implemented by taking the circuit of FIG. 2 and omitting the variable reactance 14 (and the associated control modules). The power supply of the primary conductor coil adjacent to the enclosure is adjusted to alter the power available to the pick-up using one or more of the control strategies discussed below to allow the power requirements of the biosensor to be met. The enclosure may be provided with a number of different primary conductor coils, such as the enclosure shown in FIG. 6b, 6d or 6e for example. For any independent pick-up with a single pick-up coil, best power transfer is achieved when the magnetic field vector is oriented correctly with the pick-up coil. This may be achieved by energising a plurality of primary coils (usually by different amounts) at the same time. This is equivalent to steering the orientation of the vector to best match the pick-up coil orientation. Therefore, the vector may be steered dependent on pick-up location or orientation. When multiple, independent pick-ups are to be energised, a time division multiplexing scheme can be used in the primary controller to first generate a magnetic field vector steered to match the first pick-up, then next generate a magnetic field vector steered to match the next pick-up in the next time slot. Furthermore, if the feedback control discussed above is implemented, then the orientation of the field vector, magnitude of the field vector, or frequency of oscillation of the magnetic field can be adjusted to control the power flow to the biosensor. As another alternative, multiple coils may be energised (for example using a time division multiplexing scheme) to provide a predictable or randomly changing field within the cage to supply one or more pick-ups with a single pick-up coil or a plurality of coils.

In yet another example, a number of different primary conductive paths may be provided, for example such as those shown in FIG. 6b and these may be energised using one or more power supplies such that each coil is provided at a different frequency and therefore directed to different pick-ups so that selective pick-ups within animals may be selectively powered.

In another example, the configuration in 6b may be used in such a way that a position detecting system is provided. This may be achieved by energisation of various coils to determine where the load exists for example, and once the load has been located, energising the coil nearest to which the load is present so that a localised field in the required position is provided. Position detection may also be achieved by information returned from the pick-up. Therefore, if the information on the power requirement is compared with the field being generated, then an estimate of the absolute position of the pick-up may be made for a given pick-up orientation.

Figure 10:
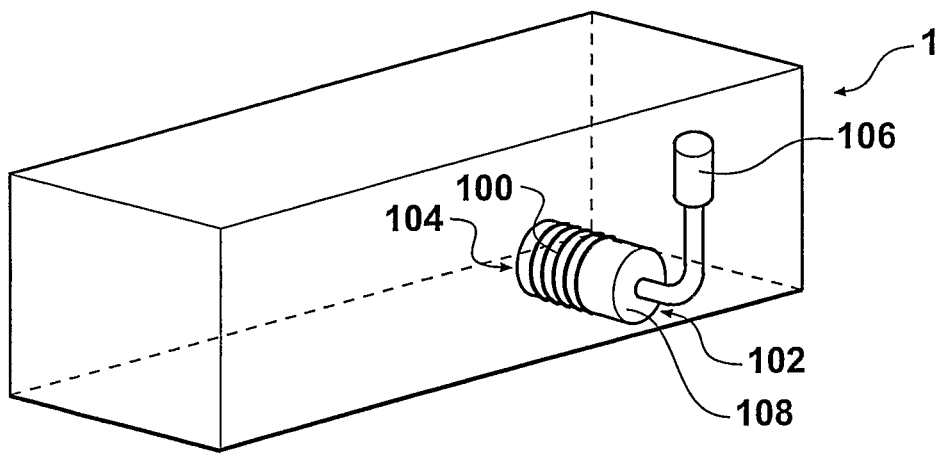
FIG. 10 is a perspective view of an animal enclosure provided with a further enclosure being a feed station
Figure 11:
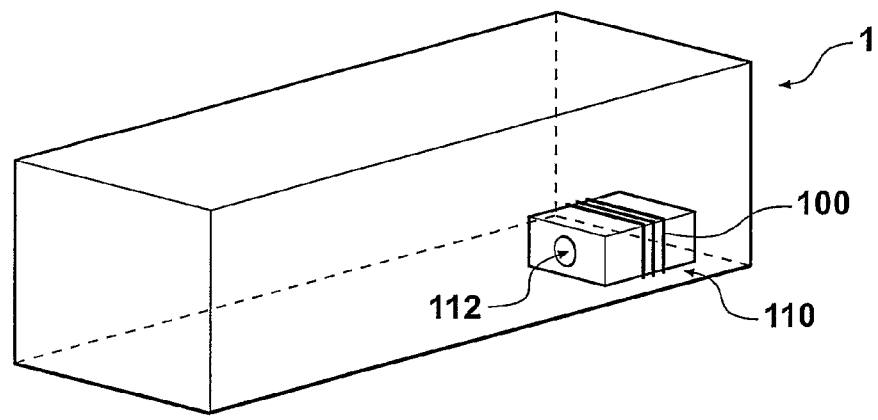
FIG. 11 is a perspective view of an animal enclosure provided with a further enclosure being a rest area

In a preferred embodiment of the invention, the pick-up that supplies power to the biosensor is mounted on a printed circuit board with a single pick-up coil. The pick-up coil in this embodiment comprises a single turn (or near turn), or multiple turns of conductive material such as copper track on or within the printed circuit board substrate. The board includes a transceiver module, and may include the biosensor itself, but is typically separately connected to the biosensor. In this embodiment, a battery may also be provided, and the battery may be mounted on the printed circuit board. A primary conductor coil system is provided about the cage or other defined space within which the biosensor is to be operable. In FIG. 10 for example the primary coil 100 is provided about an enclosure which defines a feeding station 102 which in the embodiment shown comprises a hollow cylinder with an entry 104 at one end and a water bottle 106 or similar dispensing device providing food or water through closed end 108. Similarly, as shown in FIG. 11, a primary coil 100 may be provided about an enclosure defining a rest area 110 comprising a compartment having an entry 112. FIGS. 10 and 11 illustrate that the primary coil 100 can be provided in a selected region of a larger enclosure so that the field is confined to prevent EMR problems. The pick-up does not include the de-tuning arrangement shown in FIG. 2, but the voltage supplied to the load (i.e the biosensor) is detected, and provided to the transceiver module which transmits the information to a control unit associated with the power supply for the primary coil. The control strategy illustrated with reference to FIG. 8 is then used to ensure that the pick-up is not supplying power in excess of the needs of the biosensor and associated circuits, and therefore ensure that there is no unnecessary heat being dissipated by the pick-up. The control strategy may also be used to ensure that the biosensor is receiving sufficient power.

The field is controlled to limit the power supplied to the biosensor (or to increase it if necessary) by controlling one of three different parameters, being:

a) magnetic field flux density;
b) magnetic field frequency of oscillation;
c) magnetic field vector (provided an appropriate coil configuration is provided).

Each of these parameters is discussed briefly below.

The magnetic flux density may be controlled by controlling the magnitude of the voltage applied to the primary coil. Therefore flux density can be decreased by decreasing the voltage applied to the primary coil and therefore reducing the power transferred to the pick-up.

The magnetic field frequency of oscillation is controlled by the frequency of the current provided in the primary coil. By moving the frequency of oscillation of the field toward or away from a natural resonant frequency of the pick-up (i.e. an optimal frequency of the pick-up for power transfer), more or less power will be transferred to the pick-up. It is desirable to have pick-ups with a high Q factor to improve the quality of the resonant response in the pick-up and thus maximize power transfer. A problem with using high Q circuits at a practical level is that component tolerances mean that it is difficult to provide pick-ups having the same resonant frequency. Also, component values can vary over time. Variation of field frequency also allows power to be provided to pick-ups having resonant circuits of a high Q factor. This is because the primary supply can perform a frequency sweep from a low frequency to a higher frequency, or vice versa, until feedback shows that the pick-up has been energized, and from the feedback provided by the biosensor the primary can lock onto a resonant, or near resonant, frequency of the pick-up and control the power available to it. Variation of field frequency also allows control of multiple pick-ups by providing pick-ups with distinct different resonant frequencies so that the field selectively makes power available to each pick-up.

Magnetic field vector orientation can be controlled if there is more than one primary coil by controlling the relative flux density generated by each coil to provide a resultant field vector orientation. In a preferred embodiment the vector has six degrees of freedom to characterize (using location, magnitude and orientation) the magnetic field at any instant in time.

In this preferred embodiment the primary coil is provided about only a selected portion of the enclosure. Therefore, a battery may be used to provide power to the sensor when the pick-up is out of range of the electromagnetic field. When the pick-up is within range of the electromagnetic field, the flow of power to the pick-up is controlled to meet biosensor needs and battery charging needs. When the battery is fully charged, the power flow is controlled to a reduced level which is sufficient to power the biosensor only. This strategy ensures that no excess energy is dissipated as heat.

Figure 12:
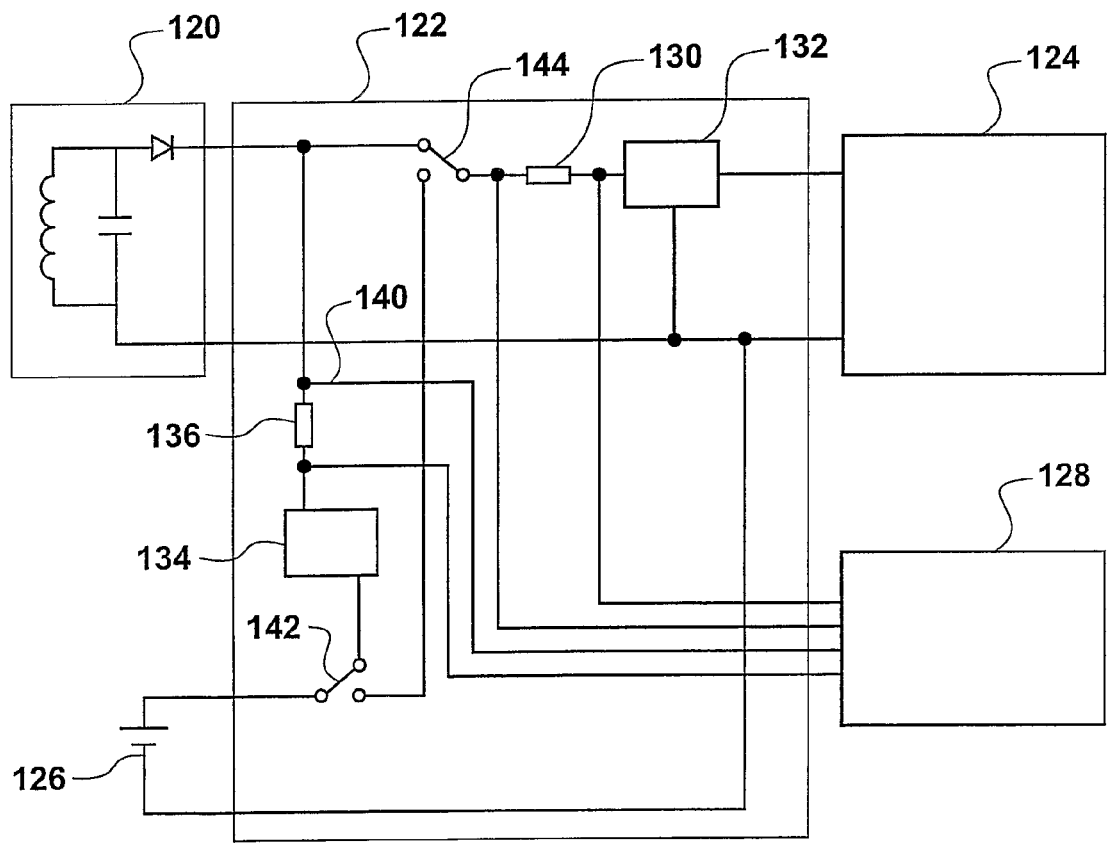
FIG. 12 is a schematic diagram illustrating the components of an inductively powered biosensor.

A diagram of the functional components of the biosensor unit of this embodiment is shown in FIG. 12 where the pick-up system 120 supplies power to a power flow controller 122 which controls the supply of power to the biosensor 124 itself, a battery 126 (if provided) and the communications module 128. Although the pick-up system is shown as having a single rectifying diode, a full bridge rectifier may be provided to increase power extraction from the pick-up resonant circuit. The power flow controller includes a sense resistor 130 which senses an indication of the power required by the biosensor (based on current drawn) and the communications module (which are supplied via voltage regulator 132). The indication of power required is provided to the communications module 128 along with the power required by the battery charger 134 which is sensed via sense resistor 136, which again allows an indication of current to be obtained. The communications module includes a microprocessor operable to provide an indication of total power demand and provide that information to a transceiver (not shown in this figure) which is part of the communications module. Line 140 senses the output voltage of the pick-up system so it can be used to provide an indication of available power to the pick-up. This information is provided to the communications module for transmission by the transceiver. Switch 142 is operable by the power flow controller to allow the battery to be charged, or connected to supply power to the unit via switch 144. The biosensor unit as a whole, as shown in FIG. 12 may be provided as a single unit or one or more components may be provided separately.

Also, there is the option of providing the pick-up with additional magnetic field coils in different orientations (as discussed with reference to FIG. 4), and it is also possible to select one of the coils 10$x$, 10$y$ or 10$z$ as the coil from which power is derived, and use the other two coils to provide feedback on the orientation of the pick-up relative to the field. Coils not used for deriving power may be specially designed for field detection. This information may be used to assist determination of the location of the pick-up, or to select the field vector required for providing the desired power flow to the pick-up.

Figure 9:
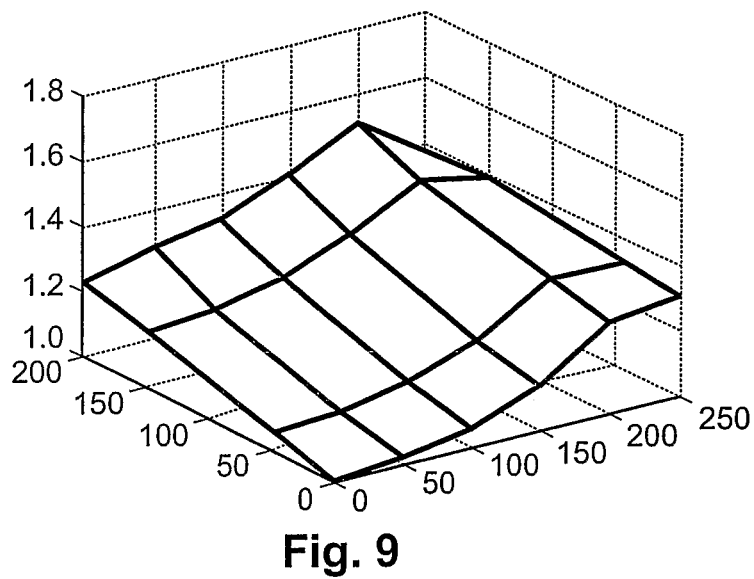
FIG. 9 is a plot of power against distance showing the power received by a pick-up in a quadrant of a space bordered by a primary conductor

Implementation of the control strategy described above is now discussed with reference to FIG. 9 and Table 1. FIG. 9 shows available power to a pick-up device located on an enclosure base within a total area size of 500 mm by 400 mm. The primary coil comprises of three turns enclosing the base area and is located 50 mm above the enclosure base similar to the concept shown in FIG. 6$c$. The power level is normalized at the coil centre, which is located at point x=0, y=0 where the power level received was equal to the power need of a biosensor with a steady power need of 13 mW. The field is symmetrical in both x and y directions, so only one quarter of the area is shown in FIG. 9. The power available to the pick-up increases as the pick-up moves from the coil centre toward the coil perimeter. There is a decrease in power available at x=250 mm caused by close proximity of the biosensor to the primary coil and changes in direction of the magnetic flux vector compared to the center point. The pick-up used consists of a single coil formed using tracks on a printed circuit board of dimension 20 mm by 40 mm. The pick-up, and the energisation of the primary coil are set to deliver 13 mW of power at x=0, y=0 to match the power requirement of the biosensor. Those skilled in the art will appreciate that the power supplied to the biosensor system in excess of 13 mW is power that will be dissipated as heat within the pick-up unless the power level of the pick-up is controlled so that the power supplied to the pick-up is reduced as the pick-up moves away from point x=0, y=0 toward the coil at the perimeter.

Referring now to Table 1, the first pair of columns define the location of the pick-up and the remaining three columns show the frequency, voltage or vector orientation required to supply the pick-up with power to match the biosensor requirements at the defined location. Therefore, for example, if the pick-up is located at point x=0, y=0, then the frequency of the field is 200 kHz to supply the required 13 mW, the voltage applied to the primary 60.4 V, and the angle of the primary magnetic field vector with respect to the normal of the pick-up coil is 0°. The reference (dno) refers to "data not obtained".

TABLE 1

| Location x (mm) | Location y (mm) | Frequency (KHz) | Voltage Control (Volts DC) | Vector Control (degrees) |
|---|---|---|---|---|
| 0 | 0 | 200 | 60.4 | 0 |
| 100 | 0 | 171 | 57.1 | 27.5 |
| 200 | 0 | 153 | 48.4 | 45 |
| 0 | 100 | 160 | 51.6 | 35 |
| 100 | 100 | dno | 49.4 | 34 |
| 200 | 100 | dno | 44 | dno |

If the location of the pick-up is changed to x=100 mm, y=0 mm, then with the voltage control being 60.4 V and the vector control being 0°, then the frequency of 171 kHz will reduce the power supplied to the pick-up back to the normalized level i.e back to the 13 mW. Similarly, if at location x=100 mm, y=0 mm, the frequency may be maintained at 200 kHz and the voltage in the primary coil reduced to 57.1 V while retaining the vector control 0° to reduce the power supply to the pick-up to the normalized level. Again, at X=100 mm, Y=0 mm, the frequency may be maintained at 200 kHz, and the voltage on a primary coil maintained at 60.4 V, but if the vector can be changed to 27.5° relative to the normal of the pick-up, then the power supplied to the pick-up will be controlled to the required level.

Those skilled in the art will realize that control of the electromagnetic field as discussed above means that power flow to the pick-up can be effectively regulated even when the field is disrupted by addition of objects into the enclosure. For example the addition of a metal object into the enclosure will shift resonant frequencies, but the feedback discussed above will allow the frequency of the field to be adjusted to compensate. Therefore, the invention is robust to environmental changes independent of the biosensor configuration and/or the primary configuration.

Whilst the invention has been described with particular reference to biosensors, it will be appreciated that the system and sensors of the invention, which enable the control of power flow to sensors powered inductively, may equally have application outside the field of biology. For example, in other circumstances where there are arbitrary and variable relationships between the sensor(s) and the primary power supply and where it is necessary to avoid heat generation in the sensors, such as in small or miniaturised industrial sensors.

Those skilled in the art will realize that the sensor may sense multiple parameters and may also be associated with an actuator. Examples of actuator function include mechanical output (e.g pumps and release mechanisms), ultrasonic transducers and electrical stimulation. With such sensor/actuator systems power may be supplied through the same primary induction power system.

The invention advantageously allows frequency, voltage and vectoring of the field to be varied on the primary side and detuning to be used on the pick-up side to allow effective control of the power available to, or supplied by, the pick-up. Those skilled in the art will appreciate that these control parameters may be used in any desired combination. For example, primary frequency tuning may be used to find the resonant frequency of the pick-up, after which primary voltage variation (or pick-up detuning) may be used to match power flow to immediate power need.

It should be noted that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be included within the present invention.

Throughout this document the word "comprise" and variations such as "comprises" and "comprising" is intended to be interpreted in an inclusive sense.

The invention claimed is:

1. An inductive power transfer system, the system comprising:
   a plurality of primary conductive paths operable to provide an electromagnetic field in a defined space;
   an inductive power pick-up associated with a sensor, the pick-up having a pick-up resonant circuit, and being moveable in relation to the primary conductive paths and being capable of receiving power from the field to supply the pick-up irrespective of a location and/or orientation of the pick-up within the defined space;
   a first sensing unit operable to sense a power available to the pick-up;
   a second sensing unit operable to sense an immediate power requirement of the pick-up; and
   a control unit operable to control a frequency of oscillation of the electromagnetic field relative to a resonant frequency of the pick-up resonant circuit, and control a relative energization of the plurality of primary conductive paths to vary a vector orientation of the electromagnetic field at or adjacent the inductive power pick-up to match the power available with the immediate power requirement.

2. The inductive power transfer system of claim 1, wherein the first sensing unit is operable to sense the power available to the pick-up by sensing a voltage provided by the pick-up.

3. The inductive power transfer system of claim 1, wherein the control unit increases or decreases power available so that the power supplied to the sensor substantially matches the immediate power required by the sensor to avoid overheating.

4. The inductive power transfer system of claim 3, wherein the second sensing unit is operable to sense the immediate power requirement by sensing a current drawn.

5. The inductive power transfer system of claim 1, further comprising a transmission unit operable to transmit the available power at the pick-up to the control unit.

6. The inductive power transfer system of claim 3, further comprising a transmission unit operable to transmit the available power at the pick-up and the immediate power requirement to the control unit.

7. The inductive power transfer system of claim 5, wherein the sensor is a biosensor and the transmission unit is further operable to transmit physiological data sensed by the biosensor.

8. The inductive power transfer system of claim 1, further comprising a plurality of sensors, each sensor having a separate pick-up associated therewith, wherein the control unit varies the field vector orientation at or adjacent each pick-up to selectively make power available to each pick-up.

9. The inductive power transfer system of claim 1, wherein the control unit is operable to increase or decrease a current or voltage supplied to each of said plurality of primary conductive paths.

10. The inductive power transfer system of claim 1, wherein the control unit is operable to energize each of the plurality of primary conductive paths individually by different amounts at the same time.

11. The inductive power transfer system of claim 1, wherein the control unit is operable to detect a position of the pick-up within the defined space and energize the primary conductive path nearest the detected position of the pick-up to generate a localized electromagnetic field.

12. The inductive power transfer system of claim 1, wherein the pick-up comprises only a single coil.

13. A method of inductive power transfer provided in a defined space, the method comprising:
generating an electromagnetic field in the defined space using one or more of a plurality of conductive paths;
receiving power from the field at a pick-up associated with a sensor and comprising a pick-up resonant circuit, irrespective of a location and/or orientation of the pick-up within the defined space, the pick-up being moveable in relation to the primary conductive paths;
sensing a power available to the pick-up provided in the defined space;
sensing an immediate power requirement of the pick-up, and
controlling a frequency of oscillation of the electromagnetic field relative to a resonant frequency of the pick-up resonant circuit, and controlling a relative energization of the plurality of primary conductive paths to vary a vector orientation of the electromagnetic field at or adjacent the pick-up to match the power available with the immediate power requirement.

14. The method of claim 13, wherein the controlling step comprises increasing or decreasing a current or voltage supplied to at least one of said plurality of primary conductive paths.

15. The method of claim 13, further comprising:
providing a plurality of sensors each associated with a separate pick-up; and
varying the field vector orientation at or adjacent each pick-up to selectively make power available to each sensor.

16. The method of claim 13, wherein controlling the field comprises energizing the plurality of primary conductive paths by different amounts at the same time.

17. The method of claim 13, further comprising:
detecting a position of the pick-up within the defined space; and
energizing the primary conductive path nearest the detected position of the pick-up to generate a localized electromagnetic field.

18. An animal enclosure comprising:
a perimeter defined by one or more walls, a floor and/or a ceiling;
a plurality of conductive paths operable to provide an electromagnetic field in the space defined by the perimeter of the enclosure; and
a power supply operable to energize the primary conductive paths to transfer power to a moveable inductive power pick-up located within the defined space and irrespective of a location and/or orientation of the pick-up relative to the primary conductive paths, the inductive power pick-up comprising a pick-up resonant circuit and being associated with a sensor, the inductive power pick-up further comprising a first sensing unit operable to sense a power available to the pick-up and a second sensing unit operable to sense an immediate power requirement of the pick-up, wherein the power supply is operable to control a frequency of oscillation of the electromagnetic field relative to a resonant frequency of the pick-up resonant circuit and control a relative energization of the plurality of primary conductive paths to vary a vector orientation of the electromagnetic field at or adjacent the pick-up to match the power available with the immediate power requirement.

19. The animal enclosure of claim 18, wherein the plurality of coplanar primary conductive paths are arranged along one of said walls, floor or ceiling of the enclosure.

20. The animal enclose of claim 19, wherein the plurality of coplanar primary conductive paths are arranged along the floor of the enclosure.

21. The animal enclosure of claim 18, wherein the enclosure comprises a cage.

22. The animal enclosure of claim 18, wherein each primary conductive path comprises a multi-turn coil.

23. The animal enclosure of claim 18, further comprising a radio frequency receiver operable to receive information transmitted by a sensing device in the enclosure.

24. An inductive power supply comprising a plurality of conductive paths capable of providing an electromagnetic field in a defined space and being configured to transfer power to a moveable inductive power pick-up located within the defined space irrespective of the location and/or orientation of the pick-up relative to the primary conductive paths, wherein the power supply may be adjusted to control a frequency of oscillation of the electromagnetic field relative to a resonant frequency of the pick-up and control energization of the plurality of primary conductive paths to vary a vector orientation of the electromagnetic field at or adjacent the pick-up to match a sensed power available to the pick-up with an immediate power requirement.

\* \* \* \* \*